United States Patent [19]
Nuss, Jr. et al.

[11] 4,198,349
[45] Apr. 15, 1980

[54] BENZYLIDENEANILINE DERIVATIVES

[75] Inventors: George W. Nuss, Jr., Lansdale; Norman J. Santora, Roslyn; George H. Douglas, Malvern, all of Pa.

[73] Assignee: William H. Rorer, Inc., Fort Washington, Pa.

[21] Appl. No.: 945,827

[22] Filed: Sep. 26, 1978

Related U.S. Application Data

[63] Continuation-in-part of Ser. No. 839,960, Oct. 6, 1977, Pat. No. 4,176,198.

[51] Int. Cl.$^2$ ............................................. C07C 119/10
[52] U.S. Cl. ............................ 260/566 F; 260/465 E; 560/35; 562/440; 424/330
[58] Field of Search ........... 260/465 E, 566 R, 566 F; 560/35

[56] References Cited

U.S. PATENT DOCUMENTS

| 3,833,606 | 9/1974 | Mohan | 260/566 F X |
| 3,862,833 | 1/1975 | Johnson et al. | 260/566 F X |
| 4,047,803 | 9/1977 | Yaguchi et al. | 260/566 F X |
| 4,122,026 | 10/1978 | Osman | 260/566 R X |

OTHER PUBLICATIONS

Kadaba et al., J. Heter. Chem., vol. 4, pp. 301–304 (1967).
Goetz, J. Heter. Chem., vol. 5, pp. 501–507 (1968).
Bellobono et al., Tetrahedron, vol. 25, pp. 57–71 (1969).
Ogata et al., J. Chem. Soc. Perkin Trans., vol. 2, pp. 1792–1797 (1972).
Favini et al., Gazz. Chim. Ital., vol. 96, pp. 1423–1431 (1966).

Primary Examiner—Dolph H. Torrence
Attorney, Agent, or Firm—Miller & Prestia

[57] ABSTRACT

This invention describes a method of treating inflammation in warm blooded animals by topically administering an effective amount of benzylideneaniline or its derivatives.

2 Claims, No Drawings

BENZYLIDENEANILINE DERIVATIVES

This application is a continuation-in-part of our co-pending application Ser. No. 839,960, filed Oct. 6, 1977; now U.S. Pat. No. 4,176,198.

SUMMARY OF THE INVENTION

This invention describes novel compounds, the pharmaceutical compositions thereof and method of treating warm-blooded animals for the relief of inflammation and associated symptoms and the treatment of radiation induced erythemas by the topical administration of a benzylidene aniline or its derivatives. Additionally, the compounds of this invention have been found to be effective sunscreening agents which prevent further erythemas from occurring.

Continuous studies have been carried out during the last decade to develop drugs for topical application which would significantly inhibit the development of inflammation as well as accompanying symptoms. While this effort has been carried out in the steroidal field, there have been few compounds developed which are non-steroidal. While many anti-inflammatory compounds have been found to be effective orally, they have had the drawback of being inactive topically as well as causing various side effects or being effective only on a specific disorder.

We have also found that these compounds are effective in the treatment of inflammation and control of arthritic conditions associated with inflammation. Also, it has been found that the compounds of this invention not only are useful in treating erythemas produced by the ultraviolet rays of sunlight or artificial light, but prevent further erythemas from occurring.

This invention describes a new method of treating inflammation of the integument in warmblooded animals by the topical administration of a compound having the structural formula as shown in FIG. 1.

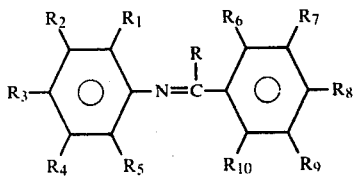

where:
R is hydrogen or alkyl;
$R_1$, $R_2$, $R_3$, $R_4$, $R_5$, $R_6$, $R_7$, $R_8$, $R_9$ and $R_{10}$ may be the same or different and are
hydrogen,
alkyl,
cyano,
nitro,
amino,
haloloweralkoxy,
haloloweralkyl,
halo,
loweralkoxy,
acyl,
acyloxy,
thio,
acylthio,
loweralkylthio,
loweralkylsulfinyl,
loweralkylsulfonyl; and hydroxy,
$R_3$ and $R_8$ may also be cycloalkyl, cycloalkenyl, aryl and heteroloweralkylidenyl, and
$R_6$, $R_7$, $R_8$, $R_9$, and $R_{10}$ may also be carboxy and carbalkoxy.

The novel compounds of the present invention which have been found to possess anti-inflammatory activity are the compounds of the formula:

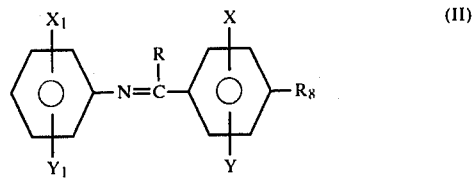

where R is hydrogen or alkyl; X and Y may be the same or different and are hydrogen, alkyl, cyano, nitro, amino, haloloweralkoxy, haloloweralkyl, halo, acyl, acyloxy, thio, acylthio, loweralkylthioloweralkylsulfinyl, loweralkylsulfonyl, and hydroxy; $X_1$ and $Y_1$ are the same or different and are hydrogen, alkyl, halo, loweralkylthio, nitro, carboxy, carbalkoxy, loweralkylsulfinyl, and loweralkylsulfonyl; $R_8$ may also be hydrogen, nitro, alkylsulfonyl, cyano, crboxy, carbalkoxy, cycloalkyl, cycloalkenyl, aryl and heteroloweralkylidenyl, and with the provisio that at least two of $R_8$, X, $X_1$, Y and $Y_1$ are other than hydrogen, and when both $X_1$ and $Y_1$ are halo, X and Y are not halo, and further when $R_8$ is cyano, $X_1$ and $Y_1$ are other than alkyl.

More particularly, the novel compounds which have been found to possess anti-inflammatory properties as well as being effective in treating radiation induced erythemas are the N-(halobenzlidene)halo-loweralkylaniline, i.e. N-(o-chlorobenzylidene)-3-chloro-2-methylaniline; N-(2-loweralkylhalobenzylidene)-hydroxyaniline, i.e. N-(2-methyl-3-chlorobenzylidene)-2-haloaniline; N-(cyanobenzylidene)-dihaloaniline, i.e. N-(p-cyanobenzylidene)-3,5-dichloroaniline; N-(nitrobenzylidene)-dihaloaniline i.e. N-(p-nitrobenzylidene)-3,5-dichloroaniline; N-(halobenzylidene) loweralkylhaloaniline, i.e. N-(p-chlorobenzylidene)-2-methyl-3-chloroaniline; N-(carbalkoxybenzylidene)-dihaloaniline, i.e. N-(p-carbomethoxybenzylidene)-3,5-dichloroaniline; N-(m-halobenzylidene)-4-haloaniline, i.e. N-(m-chlorobenzylidene)-4-fluoroaniline; N-(benzylidene)-3,5-dichloroaniline; N-(loweralkylsulfonylbenzylidene)-3,5-dihaloaniline, i.e. N-(p-methylsulfonylbenzylidene)-3,5-dichloroaniline.

In the descriptive portions of this invention, the following definitions apply:

"alkyl" refers to a loweralkyl hydrocarbon group containing from 1 to about 7 carbon atoms which may be straight chained or branched;

"alkenyl" refers to an unsaturated or partially unsaturated hydrocarbon group containing from 2 to about 7 carbon atoms which may be straight chained or branched;

"cycloalkyl" refers to a hydrocarbon ring having up to about 7 carbon atoms;

"cycloalkenyl" refers to a partially unsaturated hydrocarbon ring having up to about 7 carbon atoms;

"aryl" refers to any benzenoid aromatic group but preferably phenyl;

"acyl" refers to any organic radical derived from an organic acid by the removal of its hydroxyl group such as formyl, acetyl, propionyl, 3-carboxy-2-propenoyl, camphoryl, benzoyl, toluoyl or heteroyl such as pyridinoyl, piperidonyl, thenoyl, etc.

The compounds of this invention may be prepared by the following general procedures.

Condensation of an aniline derivative with benzaldehyde derivatives or phenyl ketones along the procedures as described by Gillman and Blatt, Organic Synthesis, Coll. Vol. I, 2nd Ed., N.Y. John Wiley and Sons, pages 80-81 will result in the desired product.

The following reaction equation illustrates this synthesis:

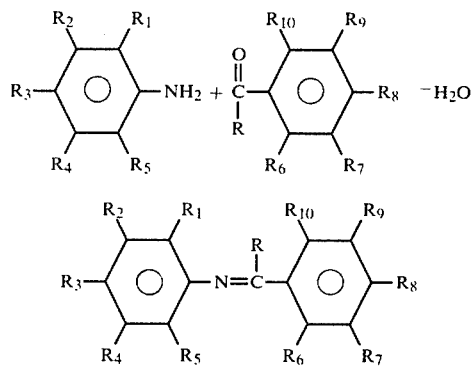

where $R$, $R_1$, $R_2$, $R_3$, $R_4$, $R_5$, $R_6$, $R_7$, $R_8$, $R_9$ and $R_{10}$ are as described above.

An alternate method of the production of certain compounds of Formula I involves the distillation of a product from a neat mixture of an aroyl compound and an aniline derivative at an elevated temperature and under a reduced pressure.

A still further method of preparing certain compounds of Formula I would be by condensation of a hindered aroyl compound and an aniline derivative by the azeotropic removal of water.

Appropriately desired end products having various substituents can be prepared at various stages of synthesis using suitable reactions in order to convert one group to another. Thus, for example, using conventional methods, a halogen group can be treated under Rosenmund Von Braun conditions to the nitrile compound. A nitro can be reduced to an amino which can be alkylated to the dialkylamino substituent. A hydroxy compound can be prepared by demethylation of a methoxy substituent. A Sandmeyer type reaction can be carried out on an amino compound to introduce a chloro, bromo, xanthate, hydroxyl or alkoxyl group. The xanthate can then lead to the mercapto by hydrolysis, this in turn can be alkylated to an alkylthio group which can be oxidized to alkylsulfinyl and alkylsulfonyl groups. A thiocyanato group may be removed by catalytic hydrogenation.

In accordance with the present invention, a method of treating warmblooded animals is provided which comprises topically administering to the warmblooded animals in need of such treatment an effective amount of a compound of Formula I.

As used herein, the term "treatment" is meant to include both active treatment and preventative or prophylactic treatment.

The present invention also has for its feature compositions for treating conditions requiring anti-inflammatory treatment containing at least one of the compounds of Formula I in an amount of about 0.05-5.0% by weight of the composition, preferably from about 0.1-1.0% by weight. These compositions can be in the form of a solution, a cream, a powder, gel, ointment, salve, lotion or milk. They can also constitute makeup products or dermatological cakes containing the ingredients standard to these types of compositions.

The concentration of active sunscreen ingredient in dermatologically-acceptable carrier preparations such as contemplated herein is between about 1.0% and about 30.0% by weight and preferably between about 2.0% and about 5.0% by weight.

The following examples will further illustrate the formulations containing the compounds of Formula I but are not to be considered as limiting the scope of this invention.

EXAMPLE 1

Testing of the anti-inflammatory effects of the compounds of Formula I were performed utilizing a modification of the experimental techniques described by Tonelli, G., Thibault, L. and Ringler, L., "A Bioassay for the Concomitant Assessment of the Anti-phlogistic and Thymolytic Activities of Topically Applied Corticoids": *Endocrinology* 77, 625 (1965) and Roszkowski, A. P., Rooks, W. H. II, Tomolonis, A. J., and Miller, L. M., "Anti-inflammatory and Analgetic Properties of the d-2-(6-Methoxy-2'-Naphthyl)Propionic Acid (Naproxen)". *J. Pharm. Exp. Ther.*, 179, 114 (1971).

The topical anti-inflammatory activity of the test compounds is measured by immediate application at the time of induction of croton oil-induced inflammation in the mouse's ear.

0.1 ml. of a solution containing 2% croton oil (Amend Drug and Chemical Co., Irvington, N.J.), 73% diethyl ether, U.S.P. (Corco Chemical Corp., Fairless Hills, Pa.), 20% pyridine (J. T. Baker Chemical Co., Phillipsburg, Pa.) and 5% distilled water was applied to the left ear of female $CF_1$ mice, in groups of six, during light ether anesthesia.

Four hours after application of either the irritant solution or the irritant solution containing the test compound, the mice were sacrificed by cervical dislocation, both ears were amputated and circular sections, one from each ear, were removed with a No. 4 cork borer (7 mm, i.d.). Each ear section was then weighed. The increase in weight due to edema formation caused by the croton oil in the treated ear and the reduction of that edema caused by drug treatment was determined by subtracting the weight of the untreated right ear section from that of the treated left ear section.

The anti-inflammatory effects of the test compounds expressed as percent inhibition are calculated by:

$$\frac{\text{Edema wt. (controls)} - \text{Edema wt. (treated)} \times 100}{\text{Edema Weight (controls)}}$$

A further test for evaluating the topical activity of these compounds involved the following procedure:

0.1 ml. of a vehicle containing 2% croton oil (Amend Drug and Chemical Co., Irvington, N.J.), N.F. VII, 20% pyridine (J. T. Baker Chemical Co., Phillipsburg, Pa.), 73% diethyl ether (Corco Chemical Corp., Fairless Hills, Pa.) and 5% distilled water is applied in 0.05 ml. aliquots, one each to the anterior and the posterior surfaces of the left ear. Drugs to be tested are dissolved or suspended in a vehicle containing 75% diethyl ether, 20% pyridine and 5% water so that each drug dose is contained in 0.1 ml. of the vehicle. The drug is applied one hour after application of vehicle containing the croton oil. Both applications are performed during ether anesthesia.

Three hours after drug application the mice are sacrificed by cervical dislocation and both ears are removed. Circular sections are taken using a No. 4 cork borer. The increase in weight caused by the irritant is found by subtracting the weight of the untreated right ear section from that of the left ear section. Drug effects expressed as percent inhibition are determined by:

$$\frac{\text{Weight Increase of Controls} - \text{Weight Increase of Treatment}}{\text{Weight Increase of Controls}} \times 100$$

The representative results of the tests are noted in the following Table:

TABLE I
TOPICAL ANTI-INFLAMMATORY ACTIVITY AFTER IMMEDIATE APPLICATION IN CROTON OIL-INDUCED INFLAMMATION IN THE MOUSE'S EAR

| Compound | Topical Dose (mg/ear) | % Inhibition of Ear Edema |
|---|---|---|
| N-benzylidene-p-toluidine | 4 | 45.0 |
| N-(o-hydroxybenzylidene)-aniline | 4 | 5.3 |
| N-(o-hydroxybenzylidene)-m-(α,α,α-trifluorotoluidine) | 4 | 21.6 |
| N-benzylideneaniline | 4 | 4.9 |
| N-benzylidene-p-ethylaniline | 4 | 30.5 |
| N-(o-hydroxybenzylidene)-2-methyl-3-chloroaniline | 4 | 38.5 |
| N-(o-hydroxybenzylidene)-2,3-dimethylaniline | 4 | 27.8 |
| N-(m-chlorobenzylidene)-p-fluoroaniline | 4 | 9.1 |
| N-benzylidene-p-chloroaniline | 4 | 29.3 |
| N-(o-hydroxybenzylidene)-p-fluoroaniline | 4 | 21.5 |
| N-(p-chlorobenzylidene)-p-fluoroaniline | 4 | 45.2 |
| N-(p-phenylbenzylidene)-p-bromoaniline | 4 | 25.5 |
| N-(o-chlorobenzylidene)-p-fluoroaniline | 4 | 24.3 |
| N-benzylidene-2-methyl-4-fluoroaniline | 4 | 26.8 |
| N-(p-chlorobenzylidene)-m-fluoroaniline | 4 | 10.8 |
| N-(p-chlorobenzylidene)-m-chloroaniline | 4 | 23.6 |
| N-(o-chlorobenzylidene)-3-chloro-2-methylaniline | 4 | 44.3 |
| N-(p-chlorobenzylidene)-2-methyl-4-chloroaniline | 4 | 23.0 |
| N-(p-phenylbenzylidene)-2-chloro-4-bromoaniline | 4 | 33.9 |
| N-(p-chlorobenzylidene)-2-methyl-3-chloroaniline | 4 | 46.8 |
| N-(3-chloro-4-cyclohexylbenzylidene)-p-fluoroaniline | 4 | 6.8 |
| N-(p-chlorobenzylidene)-4-fluoro-2-trifluoromethylaniline | 4 | 36.5 |
| N-(p-bromobenzylidene)-4-fluoro-2-trifluoromethylaniline | 4 | 18.8 |
| N-(p-fluorobenzylidene)-o-trifluoromethylaniline | 4 | 21.3 |
| N-(o-chlorobenzylidene)-m-chloroaniline | 4 | 4.0 |
| N-(3-chloro-4-cyclohexylbenzylidene)-p-bromoaniline | 4 | 1.5 |
| N-(p-phenylbenzylidene)-p-methylaniline | 4 | 27.0 |
| N-(p-phenylbenzylidene)-aniline | 4 | 24.7 |
| N-(p-chlorobenzylidene)-p-methylaniline | 4 | 16.2 |
| N-(2,6-dichlorobenzylidene)-p-chloroaniline | 4 | 9.1 |
| N-benzylidene-o-toluidine | 4 | 5.5 |

EXAMPLE 2

N-Benzylideneaniline

Benzaldehyde (0.20 mole) was treated with aniline (0.20 mole) with vigorous stirring in a 1 liter Erlenmeyer Flask. After 15 mins. 33 cc of 95% ethanol was added and the reaction mixture was stirred vigorously for an additional 5 minutes. The reaction mixture was left standing at room temperature for 10 min.; then it was placed in an ice-bath for 0.5 hours. The crystals which formed were collected, washed with 95% ethanol, and air-dried. Recrystallization from 85% ethanol gave N-benzylideneaniline. m.p. 50°–51.5° C.

EXAMPLE 3

N-(o-hydroxybenzylidene)aniline o-Hydroxybenzaldehyde (0.20 mole) was treated with aniline with vigorous stirring in a 1 liter Erlenmeyer Flask. After 15 min., 33 cc of 95% ethanol was added and the reaction mixture was stirred vigorously for an additional 5 min. The reaction mixture was left standing at room temperature for 10 min., then it was placed in an ice-bath for 0.5 hour. The crystals which formed were collected, washed with 95% ethanol, and air dried. Recrystallization from 85% ethanol yielded N-(o-hydroxybenzylidene)aniline. m.p. 47°–49° C.

EXAMPLE 4

N-(o-chlorobenzylidene)-3-chloro-2-methylaniline o-Chlorobenzaldehyde (0.20 mole) was treated with 3-chloro-2-methylaniline (0.20 mole) with vigorous stirring in a 1 liter Erlenmeyer Flask. After 15 mins., 33 cc of 95% ethanol was added and the reaction mixture was stirred vigorously for an additional 5 mins. The reaction mixture was left standing at room temperature for 10 mins., then it was placed in an ice-bath for 0.5 hr. The crystals which formed were collected, washed with 95% ethanol and air dried. Recrystallization from 85% ethanol gave N-(o-chlorobenzylidene)-3-chloro-2-methylaniline. m.p. 83°–85° C.

EXAMPLE 5

N-(p-chlorobenzylidene)-2-methyl-4-chloroaniline

2-Methyl-4-chloroaniline (0.25 mole) and 4-chlorobenzaldehyde (0.25 mole) were ground in a mortar. The mixture was heated, with stirring in a water bath for 1.5 hours. Distillation at reduced pressure gave N-(p-chlorobenzylidene)-2-methyl-4-chloroaniline. Bp. 139° C./0.020 mm.; m.p. 75°–76° C.

EXAMPLE 6

N-(α-methylbenzylidene)-p-toluidine p-Toluidine (0.20 mole), acetophenone (0.20 mole), and IRC-50 (weakly acidic) ion exchange resin (0.5 g.) were azeotropically refluxed in toluene (150 cc). The required amount of water had been removed after 3 hours. The solvent was removed on the rotary, and the residue was distilled under reduced pressure to give N-(α-methylbenzylidene)-p-toluidine. b.p. 129°-37° C./0.05 mm.

EXAMPLE 7

N-(o-hydroxybenzylidene)-2-methyl-3-chloroaniline o-Hydroxybenzaldehyde (0.20 mole) was treated with 2-methyl-3-chloroaniline (0.20 mole) with vigorous stirring in a 1 liter Erlenmeyer flask. After 15 mins. 33 cc of 95% ethanol was added and the reaction mixture was stirred vigorously for an additional 45 mins. The reaction mixture was left standing at room temperature for 10 min., then it was placed in an ice-bath for 0.5 hour. The crystals which formed were collected, washed with 95% ethanol, and air dried. Recrystallization from 85% ethanol gave N-(o-hydroxybenzylidene)-2-methyl-3-chloroaniline. m.p. 95°-97° C.

EXAMPLE 8

N-(p-chlorobenzylidene)-2-methyl-3-chloroaniline 2-methyl-3-chloroaniline (0.25 mole) and 4-chlorobenzaldehyde (0.25 mole) were ground in a mortar. The mixture was heated, with stirring in a water bath for 1.5 hours. Distillation at reduced pressure gave N-(p-chlorobenzylidene)-2-methyl-3-chloroaniline as a second fraction; B.p. 139° C./0.020 mm.; m.p. 79°-81° C.

EXAMPLE 9

N-(p-phenylbenzylidene)-p-methylaniline p-Toluidine (0.20 mole), 4-biphenylcarboxaldehyde (0.20 mole), and IRC-50 (weakly acidic) ion exchange resin (0.5 g.) were azeotropically refluxed in toluene (150 cc). The required amount of water had been removed after 3 hours. The solvent was removed on the rotary evaporator and the residue was recrystallized with 95% ethanol to yield N-(p-phenylbenzylidene)-p-methylaniline; m.p. 137°-139° C.

EXAMPLE 10

N-(o-chlorobenzylidene)-2,3-dichloroaniline 8.1 g. (0.05 mole) of 2,3-dichloroaniline was added to 7.0 grams (0.05 mole) of o-chlorobenzaldehyde. The reaction vessel and contents were thereafter allowed to stand at room temperature for 4 hours. During this period, the reaction mixture became a solid crystalline mass. The latter was dissolved in hot benzene and thereafter cooled to room temperature whereupon the N-(o-chlorobenzylidene)-2,3-dichloroaniline product precipitated as a crystalline solid and was recovered by filtration. This product was washed with a petroleum hydrocarbon fraction boiling at from 86° to 100° C. (Skellysolve) and air dried. The washed product has a m.p. at 99.5°-105° C.

EXAMPLE 11

N-benzylidene-3,5-dichloroaniline

To a reaction flask, equipped with a Dean-Stark trap, is added 3,5-dichloroaniline (16.2 g., 0.10 mole), benzaldehyde (10.6 g., 0.10 mole), p-toluenesulfonic acid monohydrate (0.2 g.), and toluene (100 ml.). The reaction mixture is then warmed to reflux and the water (1.65 ml.) collected by azeotroping. The cooled reaction mixture is treated with charcoal and the filtrate reduced in vacuo to give an amber oil that crystallizes on standing to give N-benzylidene-3,5-dichloroaniline which is recrystallized from pentane. m.p. 52°-53° C.

EXAMPLE 12

N-benzylidene-3,4-dichloroaniline

Equimolar amounts of 3,4-dichloroaniline and benzaldehyde are stirred together at room temperature to give a nearly quantitative yield of N-benzylidene-3,4-dichloroaniline that melts at 62°-5° C. upon recrystallization from ethanol.

EXAMPLE 13

Following the procedures of Examples 2-11, the following compounds may be prepared:
N-benzylideneaniline
N-(o-hydroxybenzylidene)aniline
N-(m-hydroxybenzylidene)aniline
N-(p-hydroxybenzylidene)aniline
N-benzylidene-o-toluidine
N-benzylidene-m-toluidine
N-benzylidene-p-toluidine
N-(o-hydroxybenzylidene)-m-toluidine
N-(o-hydroxybenzylidene)-p-toluidine
N-(o-hydroxybenzylidene)-m-α,α,α-trifluorotoluidine
N-(o-hydroxybenzylidene)-p-α,α,α-trifluorotoluidine
N-benzylidene-p-ethylaniline
N-benzylidene-o-hydroxyaniline
N-benzylidene-m-hydroxyaniline
N-benzylidene-p-hydroxyaniline
N-benzylidene-2,3-dihydroxyaniline
N-benzylidene-2,4-dihydroxyaniline
N-benzylidene-2,5-dihydroxyaniline
N-benzylidene-2,6-dihydroxyaniline
N-benzylidene-3,4-dihydroxyaniline
N-benzylidene-3,5-dihydroxyaniline
N-benzylidene-2,3,4-trihydroxyaniline
N-benzylidene-2,4,6-trihydroxyaniline
N-benzylidene-3,4,5-trihydroxyaniline
N-(o-hydroxybenzylidene)-o-hydroxyaniline
N-(m-hydroxybenzylidene)-o-hydroxyaniline
N-(p-hydroxybenzylidene)-o-hydroxyaniline
N-(o-hydroxybenzylidene)-m-hydroxyaniline
N-(m-hydroxybenzylidene)-m-hydroxyaniline
N-(p-hydroxybenzylidene)-m-hydroxyaniline
N-(o-hydroxybenzylidene)-p-hydroxyaniline
N-(m-hydroxybenzylidene)-p-hydroxyaniline
N-(p-hydroxybenzylidene)-p-hydroxyaniline
N-(2,3-dihydroxybenzylidene)-o-hydroxyaniline
N-(2,4-dihydroxybenzylidene)-o-hydroxyaniline
N-(2,5-dihydroxybenzylidene)-o-hydroxyaniline
N-(2,6-dihydroxybenzylidene)-o-hydroxyaniline
N-(3,4-dihydroxybenzylidene)-o-hydroxyaniline
N-(3,5-dihydroxybenzylidene)-o-hydroxyaniline
N-(2,3,4-trihydroxybenzylidene)-o-hydroxyaniline
N-(2,4,6-trihydroxybenzylidene)-m-hydroxyaniline
N-(3,4,5-trihydroxybenzylidene)-m-hydroxyaniline
N-(2,3-dihydroxybenzylidene)-p-hydroxyaniline
N-(2,4-dihydroxybenzylidene)-p-hydroxyaniline
N-(2,5-dihydroxybenzylidene)-p-hydroxyaniline
N-(2,6-dihydroxybenzylidene)-p-hydroxyaniline
N-(3,4-dihydroxybenzylidene)-p-hydroxyaniline
N-(3,5-dihydroxybenzylidene)-p-hydroxyaniline
N-(2,3,4-trihydroxy-benzylidene)-p-hydroxyaniline
N-(2,4,6-trihydroxybenzylidene)-p-hydroxyaniline
N-(p-morpholinobenzylidene)aniline
N-(p-phenylbenzylidene)aniline o-chlorobenzylideneaniline
m-chlorobenzylideneaniline
p-chlorobenzylideneaniline
N-benzylidene-o-chloroaniline
N-benzylidene-m-chloroaniline
N-benzylidene-p-chloroaniline
N-benzylidene-2,3-dichloroaniline
N-benzylidene-2,4-dichloroaniline
N-benzylidene-2,5-dichloroaniline
N-benzylidene-2,6-dichloroaniline
N-benzylidene-3,4-dichloroaniline
N-benzylidene-3,5-dichloroaniline
N-benzylidene-2,3,4-trichloroaniline
N-benzylidene-2,4,6-trichloroaniline
N-(o-chlorobenzylidene)-o-chloroaniline
N-(m-chlorobenzylidene)-o-chloroaniline
N-(p-chlorobenzylidene)-4-toluidine
N-(p-chlorobenzylidene)-o-chloroaniline
N-(o-chlorobenzylidene)-m-chloroaniline
N-(m-chlorobenzylidene)-m-chloroaniline
N-(p-chlorobenzylidene)-m-chloroaniline
N-(o-chlorobenzylidene)-p-chloroaniline
N-(m-chlorobenzylidene)-p-chloroaniline
N-(p-chlorobenzylidene)-p-chloroaniline
N-(o-chlorobenzylidene)-o-fluoroaniline
N-(m-chlorobenzylidene)-o-fluoroaniline
N-(p-chlorobenzylidene)-o-fluoroaniline
N-(o-chlorobenzylidene)-m-fluoroaniline
N-(m-chlorobenzylidene)-m-fluoroaniline
N-(p-chlorobenzylidene)-m-fluoroaniline
N-(o-chlorobenzylidene)-p-fluoroaniline
N-(m-chlorobenzylidene)-p-fluoroaniline
N-(p-chlorobenzylidene)-p-fluoroaniline
N-(2,3-dichlorobenzylidene)-o-chloroaniline
N-(2,4-dichlorobenzylidene)-o-chloroaniline
N-(2,5-dichlorobenzylidene)-o-chloroaniline
N-(2,6-dichlorobenzylidene)-o-chloroaniline
N-(3,4-dichlorobenzylidene)-o-chloroaniline
N-(3,5-dichlorobenzylidene)-o-chloroaniline
N-(2,3,4-trichlorobenzylidne)-o-chloroaniline
N-(2,4,6-trichlorobenzylidene)-o-chloroaniline
N-(2,3-dichlorobenzylidene)-m-chloroaniline
N-(2,4-dichlorobenzylidene)-m-chloroaniline
N-(2,5-dichlorobenzylidene)-m-chloroaniline
N-(2,6-dichlorobenzylidene)-m-chloroaniline
N-(3,4-dichlorobenzylidene)-m-chloroaniline
N-(3,5-dichlorobenzylidene)-m-chloroaniline
N-(2,3,4-trichlorobenzylidene)-m-chloroaniline
N-(2,4,6-trichlorobenzylidene)-m-chloroaniline
N-(2,3-dichlorobenzylidene)-p-chloroaniline
N-(2,4-dichlorobenzylidene)-p-chloroaniline
N-(2,5-dichlorobenzylidene)-p-chloroaniline
N-(2,6-dichlorobenzylidene)-p-chloroaniline
N-(3,4-dichlorobenzylidene)-p-chloroaniline
N-(3,5-dichlorobenzylidene)-p-chloroaniline
N-(2,3,4-trichlorobenzylidene)-p-chloroaniline
N-(2,4,6-trichlorobenzylidene)-p-chloroaniline
o-fluorobenzylideneaniline
m-fluorobenzylideneaniline
p-fluorobenzylideneaniline
N-benzylidene-o-fluoroaniline
N-benzylidene-m-fluoroaniline
N-benzylidene-p-fluoroaniline
N-benzylidene-2,3-difluoroaniline
N-benzylidene-2,4-difluoroaniline
N-benzylidene-2,5-difluoroaniline
N-benzylidene-2,6-difluoroaniline
N-benzylidene-3,4-difluoroaniline
N-benzylidene-3,5-difluoroaniline
N-(o-chlorobenzylidene)-p-trifluoromethylaniline
N-benzylidene-2,3,4-trifluoroaniline
N-benzylidene-2,4,6-trifluoroaniline
N-(o-fluorobenzylidene)-o-fluoroaniline
N-(m-fluorobenzylidene)-o-fluoroaniline
N-(p-fluorobenzylidene)-o-fluoroaniline
N-(o-fluorobenzylidene)-m-fluoroaniline
N-(m-fluorobenzylidene)-m-fluoroaniline
N-(p-fluorobenzylidene)-m-fluoroaniline
N-(o-fluorobenzylidene)-m-fluoroaniline
N-(m-fluorobenzylidene)-m-fluoroaniline
N-(p-fluorobenzylidene)-m-fluoroaniline
N-(2,3-difluorobenzylidene)-o-fluoroaniline
N-(2,4-difluorobenzylidene)-o-fluoroaniline
N-(2,5-difluorobenzylidene)-o-fluoroaniline
N-(2,6-difluorobenzylidene)-o-fluoroaniline
N-(3,4-difluorobenzylidene)-o-fluoroaniline
N-(3,5-difluorobenzylidene)-o-fluoroaniline
N-(2,3,4-trifluorobenzylidene)-o-fluoroaniline
N-(2,4,6-trifluorobenzylidene)-o-fluoroaniline
N-(2,3-difluorobenzylidene)-m-fluoroaniline
N-(2,4-difluorobenzylidene)-m-fluoroaniline
N-(2,5-difluorobenzylidene)-m-fluoroaniline
N-(2,6-difluorobenzylidene)-m-fluoroaniline
N-(3,4-difluorobenzylidene)-m-fluoroaniline
N-(3,5-difluorobenzylidene)-m-fluoroaniline
N-(2,3,4-trifluorobenzylidene)-m-fluoroaniline
N-(2,4,6-trifluorobenzylidene)-m-fluoroaniline
N-(2,3-difluorobenzylidene)-p-fluoroaniline
N-(2,4-difluorobenzylidene)-p-fluoroaniline
N-(2,5-difluorobenzylidene)-p-fluoroaniline
N-(2,6-difluorobenzylidene)-p-fluoroaniline
N-(o-chlorobenzylidene)-p-bromoaniline
N-(2,4-dichlorobenzylidene)-p-bromoaniline
N-benzylidene-2-methyl-3-chloroaniline
N-benzylidene-2-methyl-4-chloroaniline
N-benzylidine-2-methyl-3-fluoroaniline
N-benzylidene-2-methyl-4-fluoroaniline
N-(o-chlorobenzylidene)-2-methyl-3-chloroaniline
N-(o-chlorobenzylidene)-2-methyl-4-chloroaniline
N-(o-chlorobenzylidene)-2-methyl-5-chloroaniline
N-(m-chlorobenzylidene)-2-methyl-3-chloroaniline
N-(m-chlorobenzylidene)-2-methyl-4-chloroaniline
N-(p-chlorobenzylidene)-2-methyl-3-chloroaniline
N-(p-chlorobenzylidene)-2-methyl-4-chloroaniline
N-(p-chlorobenzylidene)-2-methyl-5-chloroaniline
N-(m-fluorobenzylidene)-2,4-dichloroaniline
N-(o-fluorobenzylidene)-2,4-dichloroaniline
N-(p-fluorobenzylidene)-2,4-dichloroaniline
N-(o-fluorobenzylidene)-2-methyl-3-chloroaniline
N-(o-chlorobenzylidene)-2-methyl-3-chloroaniline
N-(o-hydroxybenzylidene)-2-methyl-3-chloroaniline
N-(o-methylbenzylidene)-2-methyl-3-chloroaniline
N-(o-ethylbenzylidene)-2-methyl-3-chloroaniline
N-(p-chlorobenzylidene)-2-trifluoromethyl-4-fluoroaniline
N-(o-chlorobenzylidene)-2-trifluoromethyl-4-fluoroaniline
N-(o-chlorobenzylidene)-2-trifluoromethyl-3-fluoroaniline
N-(p-chlorobenzylidene)-2-trifluoromethyl-3-fluoroaniline
N-(p-bromobenzylidene)-2-trifluoromethyl-3-fluoroaniline
N-(p-bromobenzylidene)-2-trifluoromethyl-4-fluoroaniline N-(p-fluorobenzylidene)-2-trifluoromethyl-4-fluoroaniline
N-(p-phenylbenzylidene)-p-toluidine
N-(p-phenylbenzylidene)-p-bromoaniline
N-(p-phenylbenzylidene)-2-methyl-4-chloroaniline
N-(p-phenylbenzylidene)-2-methyl-4-fluoroaniline
N-(p-phenylbenzylidene)-2-chloro-4-bromoaniline
N-(3-chloro-4-cyclohexylbenzylidene)-4-fluoroaniline
N-(3-chloro-4-cyclohexylidene)-4-bromoaniline
N-(o-hydroxybenzylidene)-o-chloroaniline
N-(o-hydroxybenzylidene)-m-chloroaniline
N-(o-hydroxybenzylidene)-p-chloroaniline
N-(o-hydroxybenzylidene)-o-fluoroaniline
N-(o-hydroxybenzylidene)-m-fluoroaniline
N-(o-hydroxybenzylidene)-p-fluoroaniline
N-(o-hydroxybenzylidene)-2-methyl-3-chloroaniline
N-(o-hydroxybenzylidene)-2-methyl-4-chloroaniline
N-(o-hydroxybenzylidene)-2,3-dimethylaniline
N-(o-hydroxybenzylidene)-2,4-dimethylaniline
N-(o-hydroxybenzylidene)-o-toluidine
N-(o-hydroxybenzylidene)-m-toluidine
N-(o-hydroxybenzylidene)-p-toluidine
N-(benzylidene)-2,4-dibromoaniline
N-(m-fluorobenzylidene)-2,4-dibromoaniline
N-(m-fluorobenzylidene)-2-methyl-4-iodoaniline
N-(o-fluorobenzylidene)-2,4-dibromoaniline
N-(o-fluorobenzylidene)-2-methyl-4-iodoaniline
N-(m-fluorobenzylidene)-2,4-dibromoaniline
N-(m-fluorobenzylidene)-2-methyl-4-iodoaniline
N-(m-fluorobenzylidene)-3-tribluoromethyl-4-chloroaniline
N-(o-fluorobenzylidene)-3-trifluoromethyl-4-chloroaniline
N-(p-fluorobenzylidene)-3-trifluoromethyl-4-chloroaniline

EXAMPLE 14

N-(p-carbomethoxybenzylidene)-3,5-dichloroaniline p-Carbomethoxybenzaldehyde (0.20 moles) was treated with 3,5-dichloroaniline (0.20 moles) with vigorous stirring in a 1 liter Erlenmeyer Flask. After 15 mins., 33 cc. of 95% ethanol was added and the reaction mixture was stirred vigorously for an additional 5 minutes. The reaction mixture was left standing at room temperature for 10 min.; then it was placed in an ice bath for 0.5 hours. The crystals which formed were collected, washed with 95% ethanol, and air-dried. Recrystallization from 85% ethanol gave N-(p-carbomethoxybenzylidene)-3,5-dichloroaniline.

EXAMPLE 15

N-(o-carboxybenzylidene)aniline o-carboxybenzylaldehyde (0.20 moles) was treated with aniline with vigorous stirring in a 1 liter Erlenmeyer Flask. After 15 min., 33 cc. of 95% ethanol was added and the reaction mixture was stirred vigorously for an additional 5 min. The reaction mixture was left standing at room temperature for 10 min., then it was placed in an ice bath for 0.5 hours. The crystals which formed were collected, washed with 95% ethanol, and air dried. Recrystallization from 85% ethanol yielded N-(o-carboxybenzylidene)aniline.

EXAMPLE 16

N-(o-carbomethoxybenzylidene)-3-chloro-2-methylaniline o-carbomethoxybenzylaldehyde (0.20 moles) was treated with 3-chloro-2-methylaniline (0.20 moles) with vigorous stirring in a 1 liter Erlenmeyer Flask. After 15 mins., 33 cc. of 95% ethanol was added and the reaction mixture was stirred vigorously for an additional 5 mins. The reaction mixture was left standing at room temperature for 10 mins., then it was placed in an ice bath for 0.5 hours. The crystals which formed were collected washed with 95% ethanol and air dried. Recrystallization from 85% ethanol gave N-(o-carbomethoxybenzylidene)-3-chloro-2-methylaniline.

EXAMPLE 17

N-(p-carbobutoxybenzylidene)-2-methyl-4-chloroaniline 2-methyl-4-chloroaniline (0.25 moles) and p-carbobutoxybenzyldehyde (0.25 moles) were ground in a mortar. The mixture was heated, with stirring in a water bath for 1.5 hours. Distillation at reduced pressure gave N-(p-carbobutoxybenzylidene)-2-methyl-4-chloroaniline.

EXAMPLE 18

N-(o-carboxybenzylidene)-p-toluidine p-toluidine (0.20 moles), o-carboxybenzylaldehyde (0.20 moles), and IRC-50 (weakly acidic) ion exchange resin (0.5 g.) were azeotropically refluxed in toluene (150 cc.). The required amount of water had been removed after 3 hours. The solvent was removed on the rotary, and the residue was distilled under reduced pressure to give N-(o-carboxybenzylidene)-p-toluidine.

EXAMPLE 19

N-(p-carbomethoxybenzylidene)-2-methyl-3-chloroaniline p-carbomethoxybenzaldehyde (0.20 moles) was treated with 2-methyl-3-chloroaniline (0.20 moles) with vigorous stirring in a 1 liter Erlenmeyer flask. After 15 mins., 33 cc of 95% ethanol was added and the reaction mixture was stirred vigorously for an additional 45 mins. The reaction mixture was left standing at room temperature for 10 min., then it was placed in an ice bath for 0.5 hours. The crystals which formed were collected, washed with 95% ethanol, and air dried. Recrystallization from 95% ethanol gave N-(p-carbomethoxybenzylidene)-2-methyl-3-chloroaniline.

EXAMPLE 20

N-(p-carboxybenzylidene)-2-methyl-3-chloroaniline 2-methyl-3-chloroaniline (0.25 moles) and p-carboxybenzaldehyde (0.25 moles) were ground in a mortar. The mixture was heated, with stirring in a water bath for 1.5 hours. Distillation at reduced pressure gave N-(p-carboxybenzylidene)-2-methyl-3-chloroaniline as a second fraction.

EXAMPLE 21

N-(p-carbomethoxybenzylidene)-p-methylaniline p-toluidine (0.20 moles), p-carbomethoxybenzaldehyde (0.20 moles), and IRC-50 (weakly acidic) ion exchange resin (0.5 g.) were azeotropically refluxed in toluene (150 cc.). The required amount of water had been removed after 3 hours. The solvent was removed on the rotary evaporator and the residue was recrystallized with 95% ethanol to yield N-(p-carbomethoxybenzylidene)-p-methylaniline.

EXAMPLE 22

N-(o-carboxybenzylidene)-2,3-dichloroaniline 8.1 g. (0.05 moles) of 2,3-dichloroaniline was added to 0.05 moles of o-carboxybenzaldehyde. The reaction vessel and contents were thereafter allowed to stand at room temperature for 4 hours. During this period, the reaction mixture became a solid crystalline mass. The latter was dissolved in hot benzene and thereafter cooled to room temperature whereupon the N-(o-carboxybenzylidene)-2,3-dichloroaniline product precipitated as a crystalline solid and was recovered by filtration. This product was washed with a petroleum hydrocarbon fraction boiling at from 86° to 100° C. (Skellysolve) and air dried.

EXAMPLE 23

N-(p-carboxybenzylidene)-3,5-dichloroaniline

To a reaction flask, equipped with a Dean-Stark trap, is added 3,5-dichloroaniline (16.2 g., 0.10 mole), p-carboxybenzaldehyde (0.10 moles), p-toluenesulfonic acid monohydrate (0.2 g), and toluene (100 ml.). The reaction mixture is then warmed to reflux and the water (1.65 ml.) collected by azeotroping. The cooled reaction mixture is treated with charcoal and the filtrate reduced to vacuo to give an amber oil that crystallizes on standing to give N-(p-carboxybenzylidene)-3,5-dichloroaniline which is recrystallized from pentane.

EXAMPLE 24

N-(p-carboxybenzylidene)-3,4-dichloroaniline

Equimolar amounts of 3,4-dichloroaniline and p-carboxybenzaldehyde are stirred together at room temperature to give a nearly quantitative yield of N-(p-carboxybenzylidene)-3,4-dichloroaniline that is recrystallized from ethanol.

EXAMPLE 25

Following the procedures of Examples 14–24, the following compounds may also be prepared:
N-(o-carbomethoxybenzylidene)aniline
N-(m-carbomethoxybenzylidene)aniline
N-(p-carbomethoxybenzylidene)aniline
N-(carboxybenzylidene)toluidine
N-(carbophenoxybenzylidene)toluidine
N-(carboethoxybenzylidene)toluidine
N-(o-carboxybenzylidene)-α,α,α-trifluorotoluidine
N-(o-carbomethoxybenzylidene)-α,α,α-trifluorotoluidine
N-(carboxybenzylidene)ethylaniline
N-(carbomethoxybenzylidene)hydroxyaniline
N-(carboethoxybenzylidene)hydroxyaniline
N-(carbopropoxybenzylidene)hydroxyaniline
N-(p-carbomethoxybenzylidene)-2,3-dihydroxyaniline
N-(p-carbomethoxybenzylidene)-2,4-dihydroxyaniline
N-(p-carbomethoxybenzylidene)-2,5-dihydroxyaniline
N-(p-carbomethoxybenzylidene)-2,6-dihydroxyaniline
N-(p-carbomethoxybenzylidene)-3,4-dihydroxyaniline
N-(p-carbophenoxybenzylidene)-3,5-dihydroxyaniline
N-(p-carboxybenzylidene)-2,3,4-trihydroxyaniline
N-(p-carbomethoxybenzylidene)-2,4,6-trihydroxyaniline
N-(p-carbomethoxybenzylidene)-3,4,5-trihydroxyaniline
N-(2,3-dicarboxybenzylidene)aniline
N-(2,4-dicarboxybenzylidene)aniline
N-(2,5-dicarboxybenzylidene)aniline
N-(2,6-dicarboxybenzylidene)aniline
N-(3,4-dicarboxybenzylidene)-o-hydroxyaniline
N-(3,5-dicarboxybenzylidene)-o-hydroxyaniline
N-(carboxybenzylidene)fluoroaniline
N-(carbomethoxybenzylidene)fluoroaniline
N-(carboethoxybenzylidene)fluoroaniline
N-(carbopropoxybenzylidene)fluoroaniline
N-(carbophenoxybenzylidene)fluoroaniline
N-(p-carbomethoxybenzylidene)-m-fluoroaniline
N-(o-carbomethoxybenzylidene)-p-fluoroaniline
N-(m-carbomethoxybenzylidene)-p-fluoroaniline
N-(p-carbomethoxybenzylidene)-p-fluoroaniline
N-(o-carbophenoxybenzylidene)-2-bromoaniline
N-(m-carbophenoxybenzylidene)-2-bromoaniline
N-(p-carbobenzyloxybenzylidene)-2-iodoaniline
N-(o-carbobenzyloxybenzylidene)-2-iodoaniline
N-(m-carbobenzyloxybenzylidene)-2-iodoaniline
N-(p-carbobenzyloxybenzylidene)-3-iodoaniline
N-(p-carbophenoxybenzylidene)-p-chloroaniline
N-(p-carbophenoxybenzylidene)-2-chloroaniline
N-(o-carbobenzyloxybenzylidene)-3-chloroaniline
N-(m-carbophenoxybenzylidene)-3-chloroaniline
N-(p-carbobenzylbenzylidene)-3-chloroaniline
N-(o-carbophenoxybenzylidene)-3-chloroaniline
N-(m-carbobenzyloxybenzylidene)-3-chloroaniline
N-(p-carbophenoxybenzylidene)-3-fluoroaniline
N-(p-carbobenzyloxybenzylidene)-p-fluoroaniline
N-(2,3-dicarbomethoxybenzylidene)-p-hydroxyaniline
N-(2,4-dicarboxymethoxybenzylidene)-p-hydroxyaniline
N-(2,5-dicarbomethoxybenzylidene)-p-hydroxyaniline
N-(2,6-dicarbomethoxybenzylidene)-p-hydroxyaniline
N-(3,4-dicarbomethoxybenzylidene)-p-hydroxyaniline
N-(3,5-dicarbomethoxybenzylidene)-p-hydroxyaniline
N-(2,3-dicarboethoxybenzylidene)-p-hydroxyaniline
N-(2,4-dicarboethoxybenzylidene)-p-hydroxyaniline
N-(carboxybenzylidene)chloroaniline
N-(carbomethoxybenzylidene)chloroaniline
N-(carboethoxybenzylidene)chloroaniline
N-(carboxybenzylidene)-2,3-dichloroaniline
N-(carbomethoxybenzylidene)-2,4-dichloroaniline
N-(carboethoxybenzylidene)-2,5-dichloroaniline
N-(p-carbomethoxybenzylidene)-2,6-dichloroaniline
N-(p-carbomethoxybenzylidene)-3,4-dichloroaniline
N-(p-carbomethoxybenzylidene)-3,5-dichloroaniline
N-(p-carbomethoxybenzylidene)-2,3,4-trichloroaniline
N-(p-carbomethoxybenzylidene)-2,4,6-trichloroaniline
N-(p-carboxybenzylidene)-4-toluidine
N-(p-carboxybenzylidene)-2,3-difluoroaniline
N-(p-carboxybenzylidene)-2,4-difluoroaniline
N-(p-carboxybenzylidene)-2,5-difluoroaniline
N-(p-carboxybenzylidene)-2,6-difluoroaniline
N-(p-carbomethoxybenzylidene)-3,4-difluoroaniline
N-(p-carbomethoxybenzylidene)-3,5-difluoroaniline
N-(p-carbomethoxybenzylidene)-p-trifluoromethylaniline
N-(p-carboxybenzylidene)-2,3,4-trifluoroaniline
N-(p-carboxybenzylidene)-2,4,6-trifluoroaniline
N-(p-carboxybenzylidene)-p-methylsulfonylaniline
N-(p-carbomethoxybenzylidene)-p-methylsulfonylaniline N-(o-carboxybenzylidene)-2-methyl-3-chloroaniline
N-(p-carboxybenzylidene)-2-methyl-3-chloroaniline
N-(o-carbomethoxybenzylidene)-2-methyl-3-chloroaniline
N-(p-carbomethoxybenzylidene)-2-methyl-3-chloroaniline
N-(p-carbomethoxybenzylidene)-p-methylsulfinylaniline
N-(p-carboxybenzylidene)-2-trifluoromethyl-4-fluoroaniline
N-(o-carboxybenzylidene)-2-trifluoromethyl-4-fluoroaniline
N-(o-carbomethoxybenzylidene)-2-trifluoromethyl-3-fluoroaniline
N-(p-carbomethoxybenzylidene)-2-trifluoromethyl-3-fluoroaniline
N-(p-carbomethoxybenzylidene)-p-aniline
N-(p-carboxybenzylidene)-2-aminoaniline
N-(p-carboxybenzylidene)-p-aminoaniline
N-(p-carbomethoxybenzylidene)-2-methyl-4-cyanoaniline
N-(p-carbomethoxybenzylidene)-2-methyl-4-nitroaniline
N-(p-carboxybenzylidene)-2,4-dinitroaniline
N-(3-carboxy-4-cyclohexylbenzylidene)aniline
N-(3-carbomethoxy-4-cyclohexylbenzylidene)aniline
N-(p-carbomethoxybenzylidene)biphenyl-4-amine
N-(p-carboxybenzylidene)biphenyl-4-amine
N-(p-carbomethoxybenzylidene)-3-nitro-biphenyl-4-amine
N-(p-carboxybenzylidene)-3-chloro-biphenyl-4-amine
N-(p-carbomethoxybenzylidene)-3-fluoro-biphenyl-4-amine
N-(p-carboxybenzylidene)-2-methyl-biphenyl-4-amine
N-(p-carbomethoxybenzylidene)-2,3-xylidine
N-(p-carbomethoxybenzylidene)-2,4-xylidine
N-(2,5-carboxybenzylidene)fluoroaniline
N-(2,6-dicarboxybenzylidene)fluoroaniline
N-(3,4-dicarboxybenzylidene)fluoroaniline
N-(3,5-dicarboxybenzylidene)fluoroaniline
N-(2,5-dicarbomethoxybenzylidene)fluoroaniline
N-(2,6-dicarbomethoxybenzylidene)fluoroaniline
N-(2,3-dicarboxybenzylidene)chloroaniline
N-(2,4-carboxybenzylidene)chloroaniline
N-(2,5-dicarboxybenzylidene)chloroaniline
N-(2,6-dicarboxybenzylidene)chloroaniline
N-(3,4-dicarboxybenzylidene)chloroaniline
N-(3,5-dicarboxybenzylidene)chloroaniline
N-(p-carboxybenzylidene)-m-methoxyaniline
N-(p-carbomethoxybenzylidene)-m-ethoxyaniline
N-(2,3-dicarbomethoxybenzylidene)-p-methoxyaniline
N-(2,4-dicarboethoxybenzylidene)-p-ethoxyaniline
N-(2,5-dicarboxybenzylidene)-p-hydroxyaniline
N-(2,6-dicarboxybenzylidene)-p-hydroxyaniline
N-(o-carboxybenzylidene)-p-bromoaniline
N-(2,4-dicarboxybenzylidene)-p-bromoaniline
N-(dicarboxybenzylidene)-2-methyl-3-chloroaniline
N-(dicarboxybenzylidene)-2-methyl-4-chloroaniline
N-(dicarbomethoxybenzylidene)-2-methyl-3-fluoroaniline
N-(dicarbomethoxybenzylidene)-2-methyl-4-fluoroaniline
N-(2,3-dicarboxybenzylidene)-2-methyl-3-chloroaniline
N-(2,4-dicarboxybenzylidene)-2-methyl-4-chloroaniline
N-(2,6-dicarboxybenzylidene)-2-methyl-5-chloroaniline
N-(2,3-dicarbomethoxybenzylidene)-2-methyl-3-chloroaniline
N-(2,4-dicarbomethoxybenzylidene)-2-methyl-4-chloroaniline
N-(2,6-dicarbomethoxybenzylidene)-2-methyl-3-chloroaniline
N-(2,6-dicarbomethoxybenzylidene)-2-methyl-4-chloroaniline
N-(2,4-dicarbomethoxybenzylidene)-2-methyl-5-chloroaniline
N-(2,4-dicarboxybenzylidene)-2,4-dichloroaniline
N-(p-carbomethoxybenzylidene)mesidine
N-(p-carboxybenzylidene)mesidine
N-(p-carbomethoxybenzylidene)-2,4-dibromoaniline
N-(p-carboxybenzylidene)-2,4-dibromoaniline
N-(p-carbomethoxybenzylidene)-2-methyl-4-iodoaniline

EXAMPLE 26

A cream was prepared as follows:

| | |
|---|---|
| N-(2,4-dicarbomethoxybenzylidene)-3,5-dichloroaniline | 0.5 g. |
| Titanium oxide | 10.0 g. |
| Red iron oxide | 0.3 g. |
| Yellow iron oxide | 0.2 g. |
| Brown iron oxide | 0.4 g. |
| Chestnut iron oxide | 0.2 g. |

Several stearyl alcohols oxyethylenated with 33 moles of:

| | |
|---|---|
| Ethylene oxide | 7.0 g. |
| Polyglycol stearate | 6.0 g. |
| Propyl parahydroxybenzoate | 0.2 g. |
| Water, Q.S.P. | 100.0 g. |

Other creams identical to that described immediately above are prepared by replacing N-(2,4-dicarbomethoxybenzylidene)-3,5-dichloroaniline compound with any of the previously-mentioned active compounds.

EXAMPLE 27

A dermatological cleansing cake is prepared by mixing together the following components:

Esters of sodium isothionate and coprafatty acids (sold under the tradename "IGEPON A" having the formula R—COO—CH$_2$—CH$_2$—SO$_3$—Na, wherein R equals fatty acid derivatives having 12–15 carbon atoms).

Lanolin derivative

N-(p-carboxybenzylidene)-2-methyl-4-chloroaniline

Other dermatological cleansing cakes, identical to the above, are prepared by replacing N-(p-carboxybenzylidene)-2-methyl-4-chloroaniline with any one of the aforementioned active compounds.

EXAMPLE 28

A powder comprising the following mixture:

| | |
|---|---|
| Talc | 99.6 g. |
| Glycerine oleate | 3.0 g. |
| Isopropyl myristate | 7.0 g. |
| N-(p-carbomethoxybenzylidene)-2-methyl-3-chloroaniline | 0.5 g. |
| Perfume | 2.0 cc. |

Other equally effective powder compositions identical to the above are prepared except that the active ingredient N-(p-carbomethoxybenzylidene)-2-methyl-3-chloroaniline is replaced by any of the other aforementioned active compounds.

EXAMPLE 29

An anti-inflammatory composition in mild form having the following composition:

| | |
|---|---|
| Hydrogenated, ethoxylate (10 mol.) lanolin | 1.8 g. |
| Triglyceride of fatty acid of coconut | 7.0 g. |
| Cetylalcohol | 0.6 g. |
| Stearylalcohol | 0.6 g. |
| Paraffin oil (lightweight) | 5.0 g. |
| N-(p-carboxybenzylidene)-p-toluidine | 0.75 g. |
| Stearic acid | 3.0 g. |
| Demineralized water | 72.2 g. |
| Triethanolamine | 0.8 g. |
| Perfume | 0.5 g. |
| Carboxyvinylpolymer | 2.0 g. |
| Conservation agent | 2.0 g. | was manufactured as follows:

A mixture of 1.8 g. hydrogenated, ethoxylated (10 mol.) lanolin, 7.0 g. triglyceride of fatty acid of coconut, 0.6 g. cetylalcohol, 0.6 g. stearyl alcohol, 5.0 g. paraffin oil, 0.05 g. hydrocortisone and 3.0 g. of stearic acid was blended at 70° C. After addition of 0.75 g. N-(p-carboxybenzylidene)-p-toluidine, 2.0 g. carboxyvinylpolymer in 72.2 g. demineralized water were added at 70° C. with stirring to the resulting suspension. The mixture was stirred for 15 minutes and then cooled. 0.8 g. of triethanolamine and 0.5 g. of perfume were added at 60° C. and 45° C., respectively. The resulting mixture was stirred until cold and a white milk, which was stable at 3,000 rpm for one hour was obtained. Viscosity: 6,000 Cp (Brockfield, Spindel, 5, 10 rpm).

EXAMPLE 30

0.5 g. of N-(2,4-dicarboxybenzylidene)-3-chloro-2-methylaniline and 0.20 g. N-(p-carbomethoxybenzylidene)-2-methyl-3-chloroaniline are predispersed in 30.0 g. of propylene glycol. The mixture is then homogenized into 97.4 g. of finished cream, ointment or lotion following a modification of any one of the procedures described in F. W. Martin et al, *Remington's Pharmaceutical Sciences*, 14th Ed., Mack Publishing Co., Easton, Pa. (1965).

EXAMPLE 31

A dermatological cleansing cake is prepared by mixing together the following components:

Esters of sodium isothionate and coprafatty acids (sold under the tradename "IGEPON A" having the formula R—COO—CH$_2$—CH$_2$—SO$_3$—Na, wherein R equals fatty acid derivatives having 12–15 carbon atoms)
Lanolin derivative
N-(o-chlorobenzylidene-2-methyl-4-chloro)aniline Other dermatological cleansing cakes, identical to the above, are prepared by replacing N-(p-chlorobenzylidene)-2-methyl-4-chloroaniline with any one of the aforementioned active compounds.

EXAMPLE 32

A powder comprising the following mixture:

| | |
|---|---|
| Talc | 99.6 g. |
| Glycerine oleate | 3.0 g. |
| Isopropyl myristate | 7.0 g. |
| N-(o-hydroxybenzylidene) 2-methyl-3-chloroaniline | 0.5 g. |
| Perfume | 2 cc. |

Other equally effective powder compositions identical to the above are prepared except that the active ingredient N-(o-hydroxylbenzylidene)-2-methyl-3-chloroaniline is replaced by any of the other aforementioned active compounds.

EXAMPLE 33

An anti-inflammatory composition in mild form having the following composition:

| Ingredient | Weight in grams |
|---|---|
| Hydrogenated, ethoxylate (10 mol.) lanolin | 1.8 |
| Triglyceride of fatty acid of coconut | 7.0 |
| Cetylalcohol | 0.6 |
| Stearylalcohol | 0.6 |
| Paraffin oil (lightweight) | 5.0 |
| N-benzylidene-p-toluidine | 0.75 |
| Stearic acid | 3.0 |
| Demineralized water | 72.2 |
| Triethanolamine | 0.8 |
| Perfume | 0.5 |
| Carboxyvinylpolymer | 2.0 |
| Conservation agent | 2.0 | was manufactured as follows:

A mixture of 1.8 g. hydrogenated, ethoxylated (10 mol.) lanolin, 7.0 g. triglyceride of fatty acid of coconut, 0.6 g. cetylalcohol, 0.6 g. stearyl alcohol, 5.0 g. paraffin oil, 0.05 g. hydrocortisone and 3.0 g. of stearic was blended at 70° C. After addition of 0.75 g. N-benzylidene-p-toluidine, 2.0 g. carboxyvinylpolymer in 72.2 g. demineralized water were added at 70° C. with stirring to the resulting suspension. The mixture was stirred for 15 minutes and then cooled. 0.8 g. of triethanolamine and 0.5 g. of perfume were added at 60° C. and 45° C. respectively. The resulting mixture was stirred until cold and a white milk, which was stable at 3,000 Rpm for one hour was obtained. Viscosity: 6,000 Cp (Brockfield, Spindel, 5, 10 Rpm).

EXAMPLE 34

0.5 g. of N-(o-chlorobenzylidene)-3-chloro-2-methylaniline and 0.20 g. N-(o-hydroxybenzylidene)-2-methyl-3-chloroaniline are predispersed in 30.0 g. of propylene glycol. The mixture is then homogenized into 97.4 grams of finished cream, ointment or lotion following a modification of any one of the procedures described in F. W. Martin et al, "Remington's Pharmaceutical Sciences", 14th Ed., Mack Publishing Co., Easton, Pa. 1965.

We claim:
1. A compound selected from the group consisting of N-(o-chlorobenzylidene)-2-methyl-3-chloroaniline, N-(p-chlorobenzylidene)-2-methyl-4-chloroaniline and N-(p-chlorobenzylidene)-2-methyl-3-chloroaniline.
2. N-(p-chlorobenzylidene)-2-methyl-4-chloroaniline.

* * * * *